United States Patent [19]

Ramachandran

[11] Patent Number: 4,550,167

[45] Date of Patent: Oct. 29, 1985

[54] PREPARATION OF 1-ALKYL-1,4-DIHYDRO-4-OXO-7-(4-PYRIDYL)-3-QUINOLINE CARBOXYLIC ACID

[75] Inventor: Venkataraman Ramachandran, Baton Rouge, La.

[73] Assignee: Ethyl Corporation, Richmond, Va.

[21] Appl. No.: 497,027

[22] Filed: May 23, 1983

[51] Int. Cl.$^4$ .................. C07D 215/16; C07D 211/72; C07D 211/70
[52] U.S. Cl. .................................... 546/156; 546/346; 546/329
[58] Field of Search .................. 546/346, 329, 156

[56] References Cited

PUBLICATIONS

Conrow, Deductive Organic Chemistry, Addison-Wesley Pub. Co., Inc., Reading, Ma., 1966, p. 171.
Noller, Textbook of Organic Chem., W. B. Saunders Co., Philadelphia, 3rd Edition, 1966, p. 226.
Klingsberg, Pyridine and its Derivatives, Part One, Interscience Publishers, Inc., New York, 1960, p. 30.

*Primary Examiner*—Henry R. Jiles
*Assistant Examiner*—Robert C. Whittenbaugh
*Attorney, Agent, or Firm*—Donald L. Johnson; John F. Sieberth; Patricia J. Hogan

[57] ABSTRACT

Diels-Alder products obtained by reacting a haloprene with a 4-vinylpyridine, i.e., mixtures of 4-(halocyclohex-3-enyl)pyridine isomers, are reacted with a relatively strong acid, i.e., an acid having a dissociation constant of at least $1.7 \times 10^{-5}$ at 25° C., to form salts which are readily separated and/or reduced.

20 Claims, No Drawings

PREPARATION OF 1-ALKYL-1,4-DIHYDRO-4-OXO-7-(4-PYRIDYL)-3-QUINOLINE CARBOXYLIC ACID

FIELD OF THE INVENTION

This invention relates to 4-(halocyclohex-3-enyl)pyridine salts, a process for preparing them, and processes for producing derivatives thereof.

BACKGROUND

Copending application Ser. No. 300,046, filed Sept. 8, 1981, in the name of Thomas J. Walter—Walter I—discloses 4-(3-chlorocyclohex-3-enyl)pyridine, 4-(4-chlorocyclohex-3-enyl)pyridine, a process for making these compounds by a Diels-Alder reaction between chloroprene and a 4-vinylpyridine, and a process for converting them to 4-(3-chlorophenyl)pyridine and 4-(4-chlorophenyl)pyridine by catalytic dehydrogenation.

Copending application Ser. No. 495,977, filed May 19, 1983, in the name of Thomas J. Walter—Walter II—discloses processes by which 4-(4-halophenyl)pyridines, such as the 4-(4-chlorophenyl)pyridine produced in Walter I, can be converted to 4-(4-halo-3-nitrophenyl)pyridines, then to 4-(3-aminophenyl)pyridines, and ultimately to the antibacterial 1-alkyl-1,4-dihydro-4-oxo-7-pyridinyl-3-quinolinecarboxylic acids of Sterling Drug's U.S. Pat. No. 3,753,993 (Lesher et al.), U.S. Pat. No. 3,907,808 (Lesher and Carabateas), and U.S. Pat. No. 4,118,557 (Lesher).

Copending application Ser. No. 497,026, filed May 23, 1983, in the name of V. Ramachandran—Ramachandran—discloses improved processes for preparing the 4-(halocyclohex-3-enyl)pyridines and derivatives wherein a boron trifluoride catalyst is employed directly to improve the yield of 4-(halocyclohex-3-enyl)pyridine and indirectly to improve the yields of derivatives thereof.

Separately and in combination, the aforementioned copending applications disclose useful processes for preparing antibacterial agents and intermediates thereof. However, since the products of the Diels-Alder reactions of these applications, i.e., the 4-(halocyclohex-3-enyl)pyridine mixtures, are not easily separated from one another and/or reduced, there is still room for improvements in these processes.

SUMMARY OF INVENTION

An object of this invention is to provide a novel process for treating the products of a Diels-Alder reaction between a haloprene and a 4-vinylpridine.

Another object is to provide such a process which facilitates separation of the products of the reaction.

Still another object is to provide such a process which accomplishes this separation via the formation of novel compounds.

A further object is to provide such a process which permits easier reduction of the products.

These and other objects are attained by reacting the Diels-Alder products of a haloprene and a 4-vinylpyridine with an acid to form salts thereof and, when appropriate, separating and/or reducing the products.

DETAILED DESCRIPTION

The haloprene utilized in the preparation of the Diels-Alder adducts of the invention is generally chloroprene but can be any other haloprene, i.e., a 2-halobutadiene-1,3 in which the halo substituent may be chloro, bromo, fluoro, or iodo.

The 4-vinylpyridine reacted with the haloprene in the preparation of the Diels-Alder adducts is preferably 4-vinylpyridine itself but may be a ring-substituted 4-vinylpyridine bearing up to four innocuous substituents, such as alkyl, cycloalkyl, aralkyl, aryl, and aralkyl groups, optionally bearing halo, hydroxy, or amino substituents and/or optionally joined to the pyridine ring by an ether linkage; halo; cyano; carboxyl; carbalkoxy; carbamyl; nitrogen-containing heterocyclic groups, etc.—any aliphatic groups usually containing 1–6 carbons arranged in straight or branched chains.

The Diels-Alder reaction is conducted essentially in accordance with the teachings of Walter I and Ramachandran, the teachings of both of which are incorporated herein by reference. Thus, it is preferred that the reactants be employed in substantially equimolar amounts, i.e., about 0.75–2, preferably about one, molar proportion of haloprene per molar proportion of the 4-vinylpyridine, and that they be reacted together at a temperature of about 100°–150° C., preferably about 130° C., under autogenous pressure, in a suitable solvent, preferably an aromatic hydrocarbon, such as xylene, which is liquid under the reaction conditions.

It is also preferred, as in Ramachandran, that the Diels-Alder reaction be conducted in the presence of a boron trifluoride catalyst, which may be boron trifluoride itself but is usually an etherate thereof, e.g., a diethyl, dipropyl, or dibutyl, etc., etherate. When a catalyst is employed, it is most preferably a boron trifluoride/diethyl ether complex—the complex commonly known as boron trifluoride etherate. The amount of catalyst used is generally such as to provide a catalyst/4-vinylpyridine mol ratio in the range of about 1–2/1, preferably about 1.1/1.

As in Walter I and Ramachandran, the Diels-Alder reaction results in the formation of a mixture of 4-(3-halocyclohex-3-enyl)pyridine and 4-(4-halocyclohex-3-enyl)pyridine isomers in a mol ratio of about 35:65, the yield varying from the relatively low yields, i.e., about 20–30%, of Walter I to the higher yields, i.e., about 75–90%, of Ramachandran.

In accordance with the present invention, the Diels-Alder product is reacted with an acid to form salts of the components of that product, i.e., salts of both the 4-(3-halocyclohex-3-enyl)pyridine and the 4-(4-halocyclohex-3-enyl)pyridine. The acid used to form the salts may be any relatively strong acid, i.e., an acid having a dissociation constant of at least about $1.7 \times 10^{-5}$, preferably at least about $1.0 \times 10^{-1}$ at 25° C. For example, it may be an inorganic acid, such as sulfuric, nitric, hydrochloric, hydrobromic, hydrofluoric, hydroborofluoric, etc.; or it may be an organic acid, such as benzoic, methanesulfonic, acetic, chloroacetic, dichloroacetic, trichloroacetic, trifluoroacetic, etc. It is preferably hydrochloric, hydrobromic, or hydroborofluoric acid; and the most preferred acid, particularly when the salts are being formed to facilitate aromatization of the isomers formed in the Diels-Alder reaction, is hydrochloric acid.

The manner in which the acid is reacted with the Diels-Alder product is not critical, any convenient method being utilizable. However, it is frequently desirable to accomplish the salt formation by bubbling acid gas through a solution containing the Diels-Alder product or, alternatively, by stirring the product in an aqueous solution of the acid. In any case, the amount of acid employed should be at least one molar proportion per molar proportion of the Diels-Alder product.

The reaction of the acid with the Diels-Alder product results in the formation of novel salts which generally correspond to the formula:

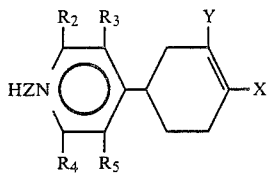

wherein HZ represents an acid; one of X and Y is halo and the other is hydrogen; and $R_2$, $R_3$, $R_4$, and $R_5$ are independently selected from hydrogen and innocuous substituents, such as alkyl, cycloalkyl, aralkyl, aryl, and alkaryl groups, optionally bearing halo, hydroxy, or amino substituents and/or optionally joined to the pyridine ring by an ether linkage; halo; cyano; carboxyl; carbalkoxy; carbamyl; nitrogen-containing heterocyclic groups, etc.—any aliphatic groups generally containing 1-6 carbons arranged in straight or branched chains.

When the salts have been formed, they may be easily separated by selective crystallization, since the salts of the 4-(4-halocyclohex-3-enyl)pyridines are much less soluble in organic solvents, such as ethanol, than the meta-isomers.

After completion of the salt formation, the salts may be separated if desired; and, as indicated above, it is one of the advantages of the invention that they are more easily separated than the isomers formed by the Diels-Alder reaction. However, as in Walter I and Ramachandran, they may be kept in admixture when they are to be aromatized to the corresponding 4-(halophenyl)pyridines; and it is another of the advantages of the invention that the salts are more readily aromatized than the adducts from which they are formed. For example, the salts may be aromatized by simply heating them in a suitable solvent, such as nitrobenzene, at an elevated temperature, such as about 195° C.

When derivatives of the 4-(halocyclohex-3-enyl)pyridine salts are desired, they may be prepared by techniques such as those taught in Ramachandran, Walter I, and Walter II. Thus, for example, the salts may be catalytically hydrogenated as in Ramachandran and Walter I to form 4-(halophenyl)pyridines; and then, when other derivatives are desired, the 4-(halophenyl)pyridines may be subjected to the appropriate reactions, e.g., the reactions taught in Walter II, the teachings of which are incorporated herein by reference.

When the processes of Walter II are to be used, the object is generally to form derivatives of the 4-(4-halophenyl)pyridine, so it may be desirable first to separate it from any 4-(3-halophenyl)pyridine with which it is in admixture. However, if desired, a crude 4-(4-halophenyl)pyridine containing a 4-(3-halophenyl)pyridine impurity may be employed in these processes.

In general, when one or more of the processes of Walter II are to be employed, the 4-(4-halophenyl)pyridine—alone or in admixture with a 4-(3-halophenyl)pyridine—is nitrated to a 4-(4-halo-3-nitrophenyl)pyridine, preferably 4-(4-chloro-3-nitrophenyl)pyridine, which may then be reduced to a 4-(3-aminophenyl)pyridine, such as 4-(3-aminophenyl)pyridine itself. Then, when antibacterial agents, such as the 1-alkyl-1,4-dihydro-4-oxo-7-pyridinyl-3-quinolinecarboxylic acids of Lesher, Lesher et al., and Lesher and Carabateas, are desired, they—of their intermediates—may be prepared by subjecting the 4-(3-aminophenyl)pyridines to suitable reactions which may be conducted by known techniques. For example:

(1) the 4-(3-aminophenyl)pyridine may be reacted with a dialkyl ethoxymethylenemalonate to form a dialkyl 3-(4-pyridyl)anilinomethylenemalonate, which may be cyclized to an alkyl 1,4-dihydro-4-oxo-7-(4-pyridyl)-3-quinolinecarboxylate, which in turn may be N-alkylated to an alkyl 1-alkyl-1,4-dihydro-4-oxo-7-(4-pyridyl)-3-quinolinecarboxylate, which may then be hydrolyzed to a 1-alkyl-1,4-dihydro-4-oxo-7-(4-pyridyl)-3-quinolinecarboxylic acid, as in Lesher et al. and Lesher and Carabateas, (2) the 4-(3-aminophenyl)pyridine may be reductively alkylated, or it may be acylated and then reduced, as in Lesher, to form a 4-(3-alkylaminophenyl)pyridine, otherwise designated as a 3-(4-pyridyl)-N-alkylaniline, which may then be (a) subjected to the reaction steps of Lesher et al. and Lesher and Carabateas without the need for their N-alkylation step or (b) subjected to reaction with a cyclic alkylidenyl alkoxymethylenemalonate, etc., as in Lesher, to form the antibacterial agent, or (3) either of the above procedures may be terminated at the end of any step to recover a desired product for use in any other desired process, etc.

As in Walter II, when an acylated 4-(3-aminophenyl)-pyridine is desired, it is sometimes convenient to combine the reduction and acylation steps, e.g., by reducing the 4-(4-halo-3-nitrophenyl)pyridine with hydrogen in the presence of sodium acetate, a palladium-on-carbon catalyst, and glacial acetic acid—a process which leads to a high yield of 4-(3-aminophenyl)pyridine at 60°–70° C. but which produces substantial yields of 4-(3-acetamidophenyl)pyridine when conducted for a sufficient time at temperatures near 80° C. Alternatively and more efficiently, 4-(3-acetamidophenyl)pyridine can be produced by including acetic anhydride in the reduction recipe.

The following examples are given to illustrate the invention and are not intended as a limitation thereof.

EXAMPLE I

A suitable reaction vessel was charged with a mixture of 31.5 g (0.3 mol) of 4-vinylpyridine, 47 g (0.33 mol) of boron trifluoride etherate, and 31 g (0.3 mol) of xylene and heated to 70° C. to distill off the ether under a nitrogen blanket. The temperature was then reduced to room temperature, and a solution of 26.5 g (0.3 mol) of cholorprene in 26.5 g (0.25 mol) of xylene was added. The reaction mixture was then heated at 130° C. for 5 hours with constant stirring, after which the xylene was removed. The residue was neutralized with 300 ml of aqueous caustic to a pH of about 7. The organic material was extracted in chloroform, and the chloroform was stripped off to isolate 51 g of a pale red oil. This oil was stirred with 330 ml of 5% aqueous hydroborofluoric acid solution to form a precipitate. Filtering of the precipitate provided a 42% yield, i.e., 34 g, of the hydroborofluoric acid salt of 4-(4-chlorocyclohex-3-enyl)pyridine.

EXAMPLE II

Forty-four grams of the Diels-Alder adduct obtained by reacting 4-vinylpyridine with chloroprene in xylene in the presence of boron trifluoride etherate were taken into ethanol and saturated with HCl. The ethanol was then evaporated to isolate a solid which was again taken into ethanol and allowed to stand overnight. After this period, 28 g of solids were filtered out, and the mother liquor was cooled to yield another 8 g of solids. The process resulted in a yield of 36 g of white 4-(4-chlorocyclohex-3-enyl)pyridine hydrochloride.

It is obvious that many variations may be made in the products and processes set forth above without departing from the spirit and scope of this invention.

I claim:

1. In a process which comprises preparing a 1-alkyl-1,4-dihydro-4-oxo-7-(4-pyridyl)-3-quinolinecarboxylic acid by (a) reacting a haloprene with a 4-vinylpyridine to form a 4-(halocyclohex-3-enyl)pyridine, including a 4-(4-halocyclohex-3-enyl)pyridine, (b) aromatizing the 4-(4-halocyclohex-3-enyl)pyridine, (c) nitrating the resultant 4-(4-halophenyl)pyridine, (d) reducing the resultant 4-(4-halo-3-nitrophenyl)pyridine to a 4-(3-aminophenyl)pyridine, (e) converting the 4-(3-aminophenyl)pyridine to an alkyl 1-alkyl-1,4-dihydro-4-oxo-7-(4-pyridyl)-3-quinolinecarboxylate, and (f) hydrolyzing the product, the improvement which comprises facilitating the aromatization of the 4-(4-halocyclohex-3-enyl)pyridine by reacting the 4-(halocyclohex-3-enyl)pyridine with an acid to form a salt prior to reducing it to a 4-(halophenyl)pyridine.

2. The process of claim 1 wherein the haloprene is chloroprene.

3. The process of claim 1 wherein the 4-vinylpyridine is 4-vinylpyridine.

4. The process of claim 1 wherein the acid is an acid having a dissociation constant of at least about $1.7 \times 10^{-5}$ at 25° C.

5. The process of claim 4 wherein the acid has a dissociation constant of at least about $1.0 \times 10^{-1}$ at 25° C.

6. The process of claim 5 wherein the acid is hydroborofluoric, hydrochloric, or hydrobromic acid.

7. The process of claim 6 wherein the acid is hydrochloric acid.

8. A 4-(halocyclohex-3-enyl)pyridine salt corresponding to the formula:

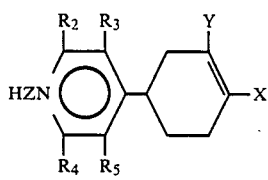

wherein HZ represents an acid; one of X and Y is halo and the other is hydrogen; and $R_2$, $R_3$, $R_4$, and $R_5$ are independently selected from hydrogen and innocuous substituents.

9. The salt of claim 8 wherein $R_2$, $R_3$, $R_4$, and $R_5$ are hydrogen, X is chloro, and HZ represents an acid having a dissociation constant of at least about $1.7 \times 10^{-5}$ at 25° C.

10. The salt of claim 9 wherein HZ represents an acid having a dissociation constant of at least about $1.0 \times 10^{-1}$ at 25° C.

11. The salt of claim 10 wherein HZ represents hydroborofluoric, hydrochloric, or hydrobromic acid.

12. The salt of claim 11 wherein HZ represents hydrochloric acid.

13. The process of claim 1 wherein:

(a) a haloprene is reacted with a 4-vinylpyridine to form a 4-(halocyclohex-3-enyl)pyridine, including a 4-(4-halocyclohex-3-enyl)pyridine,
(b) the 4-(halocyclohex-3-enyl)pyridine is reacted with an acid to form a salt, including a 4-(4-halocyclohex-3-enyl)pyridine salt,
(c) the 4-(4-halocyclohex-3-enyl)pyridine salt is reduced to a 4-(4-halophenyl)pyridine,
(d) the 4-(4-halophenyl)pyridine is nitrated to a 4-(4-halo-3-nitrophenyl)pyridine,
(e) the 4-(4-halo-3-nitrophenyl)pyridine is reduced to a 4-(3-aminophenyl)pyridine),
(f) the 4-(3-aminophenyl)pyridine is reacted with a dialkyl ethoxymethylenemalonate to form a dialkyl 3-(4-pyridyl)anilinomethylenemalonate,
(g) the dialkyl 3-(4-pyridyl)anilinomethylenemalonate is cyclized to an alkyl 1,4-dihydro-4-oxo-7-(4-pyridyl)-3-quinolinecarboxylate,
(h) the alkyl 1,4-dihydro-4-oxo-7-(4-pyridyl)-3-quinolinecarboxylate is N-alkylated to an alkyl 1-alkyl-1,4-dihydro-4-oxo-7-(4-pyridyl)-3-quinolinecarboxylate, and
(i) the alkyl 1-alkyl-1,4-dihydro-4-oxo-7-(4-pyridyl)-3-quinolinecarboxylate is hydrolyzed to a 1-alkyl-1,4-dihydro-4-oxo-7-(4-pyridyl)-3-quinolinecarboxylic acid.

14. The process of claim 13 wherein chloroprene is reacted with 4-vinylpyridine in the presence of a boron trifluoride catalyst, and the 4-(chlorocyclohex-3-enyl)pyridine product is reacted with an acid having a dissociation constant of at least $1.0 \times 10^{-1}$ at 25° C. to form a salt.

15. The process of claim 14 wherein the acid is hydroborofluoric, hydrochloric, or hydrobromic acid.

16. The process of claim 15 wherein the acid is hydrochloric acid.

17. The process of claim 1 wherein:

(a) a haloprene is reacted with a 4-vinylpyridine to form a 4-(halocyclohex-3-enyl)pyridine, including a 4-(4-halocyclohex-3-enyl)pyridine,
(b) the 4-(halocyclohex-3-enyl)pyridine is reacted with an acid to form a salt, including a 4-(4-halocyclohex-3-enyl)pyridine salt,
(c) the 4-(4-halocyclohex-3-enyl)pyridine salt is reduced to a 4-(4-halophenyl)pyridine,
(d) the 4-(4-halophenyl)pyridine is nitrated to a 4-(4-halo-3-nitrophenyl)pyridine,
(e) the 4-(4-halo-3-nitrophenyl)pyridine is reduced to a 4-(3-aminophenyl)pyridine,
(f) the 4-(3-aminophenyl)pyridine is converted to a 3-(4-pyridyl)-N-alkylaniline,
(g) the 3-(4-pyridyl)-N-alkylaniline is reacted with a dialkyl ethoxymethylenemalonate to form a dialkyl 3-(4-pyridyl)-N-alkylanilinomethylenemalonate,
(h) the dialkyl 3-(4-pyridyl-N-alkylanilinomethylenemalonate is cyclized to an alky 1-alkyl-1,4-dihydro-4-oxo-7-(4-pyridyl)-3-quinolinecarboxylate, and
(i) the alkyl 1-alkyl-1,4-dihydro-4-oxo-7-(4-pyridyl)-3-quinolinecarboxylate is hydrolyzed to a 1-alkyl-1,4-dihydro-4-oxo-7-(4-pyridyl)-3-quinolinecarboxylic acid.

18. The process of claim 17 wherein chloroprene is reacted with 4-vinylpyridine in the presence of a boron trifluoride catalyst, and the 4-(chlorocyclohex-3-enyl)pyridine product is reacted with an acid having a dissociation constant of at least $1.0 \times 10^{-1}$ at 25° C.

19. The process of claim 18 wherein the acid is hydroborofluoric, hydrochloric, or hydrobromic acid.

20. The process of claim 19 wherein the acid is hydrochloric acid.

* * * * *